US012023222B2

United States Patent
Kato et al.

(10) Patent No.: US 12,023,222 B2
(45) Date of Patent: Jul. 2, 2024

(54) VESTIBULAR STIMULATION DEVICE, DIZZINESS TREATMENT DEVICE, AND HEALTH PROMOTION DEVICE

(71) Applicant: National University Corporation Tokai National Higher Education and Research System, Nagoya (JP)

(72) Inventors: Masashi Kato, Nagoya (JP); Nobutaka Ohgami, Nagoya (JP); Michihiko Sone, Nagoya (JP); Satofumi Sugimoto, Nagoya (JP); Masashi Kato, Nagoya (JP)

(73) Assignee: NATIONAL UNIVERSITY CORPORATION TOKAI NATIONAL HIGHER EDUCTION AND RESEARCH SYSTEM, Nagoya (JP)

( * ) Notice: Subject to any disclaimer, the term of this patent is extended or adjusted under 35 U.S.C. 154(b) by 881 days.

(21) Appl. No.: 17/059,127

(22) PCT Filed: May 31, 2019

(86) PCT No.: PCT/JP2019/021688
§ 371 (c)(1),
(2) Date: Nov. 25, 2020

(87) PCT Pub. No.: WO2019/230941
PCT Pub. Date: Dec. 5, 2019

(65) Prior Publication Data
US 2021/0205137 A1    Jul. 8, 2021

(30) Foreign Application Priority Data
May 31, 2018    (JP) ................................ 2018-104637

(51) Int. Cl.
*A61F 11/00*    (2022.01)

(52) U.S. Cl.
CPC .................................. *A61F 11/00* (2013.01)

(58) Field of Classification Search
CPC ............................................ A61M 2021/0027
See application file for complete search history.

(56) References Cited

U.S. PATENT DOCUMENTS 10,232,139 B1 *    3/2019   Hang .................... A61M 21/00
2012/0059362 A1    3/2012   Ono
(Continued)

FOREIGN PATENT DOCUMENTS

CN    102144914 A    8/2011
CN    104125845 A    10/2014
(Continued)

OTHER PUBLICATIONS

An International Preliminary Report on Patentability dated Dec. 1, 2020 in PCT/JP2019/021688 is attached w/English translation, 13 pages.

(Continued)

*Primary Examiner* — Thaddeus B Cox
(74) *Attorney, Agent, or Firm* — MUNCY, GEISSLER, OLDS & LOWE, P.C.

(57) ABSTRACT

A setting unit sets a sound stimulation. A sound generation unit generates the sound stimulation thus set. The setting unit sets a sound stimulation having a sound volume level of a value between 70 and 85 decibels and a frequency of a value between 20 and 140 hertz, as a sound stimulation for activating a vestibular function via an ear stone of a subject person. The information acquisition unit acquires status information related to the vestibular function of the subject person, and the setting unit sets at least one of the sound volume level or a frequency of the sound stimulation in accordance with the information related to the vestibular function thus acquired.

20 Claims, 21 Drawing Sheets

(56) References Cited

U.S. PATENT DOCUMENTS

| | | | |
|---|---|---|---|
| 2013/0225915 A1 | 8/2013 | Redfield et al. | |
| 2016/0089298 A1 | 3/2016 | Owen | |
| 2017/0245555 A1* | 8/2017 | Karp | A47G 9/083 |
| 2018/0133102 A1 | 5/2018 | Owen et al. | |
| 2019/0022347 A1* | 1/2019 | Wan | A61B 5/18 |

FOREIGN PATENT DOCUMENTS

| | | | |
|---|---|---|---|
| CN | 104799999 A | | 7/2015 |
| DE | 102017126432 A1 | * | 5/2019 |
| EP | 2636392 A1 | | 9/2013 |
| WO | WO-2017/040747 A1 | | 3/2017 |
| WO | WO-2017040741 A1 | | 3/2017 |
| WO | WO-2018/089994 A1 | | 5/2018 |

OTHER PUBLICATIONS

Kawashima et al., "Mechanotransduction in mouse inner ear hair cells requires transmembrane channel-like genes," The Journal of Clinical Investigation, vol. 121, No. 12, Dec. 2011, 15 pages.
International Preliminary Report on Patentability dated Dec. 1, 2020 in PCT/JP2019/021688, 13 pages.
Japanese Office Action dated Aug. 9, 2022 in application No. 2020-522624; pp. 1-8.
Search Report issued Dec. 21, 2021 for corresponding European Patent Application No. 19811002.5, 8 pages.

* cited by examiner

WITHOUT SOUND STIMULATION

WITH SOUND STIMULATION

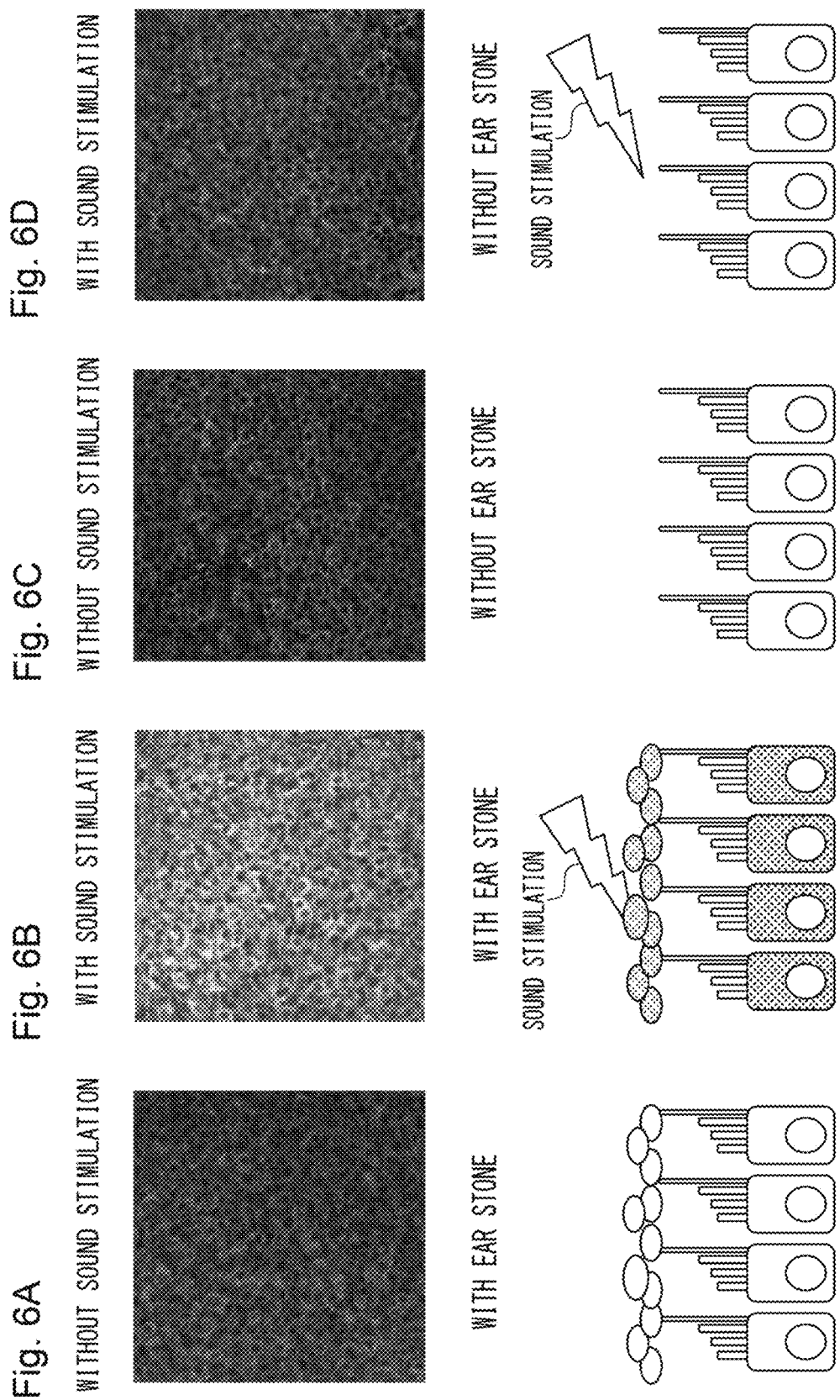

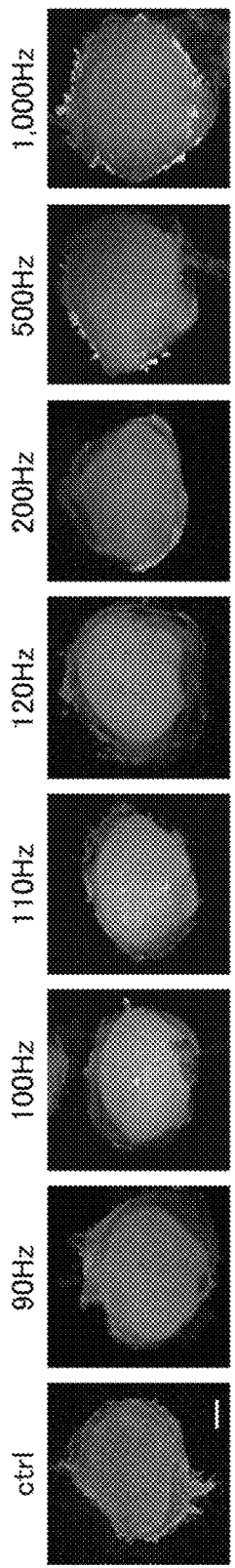
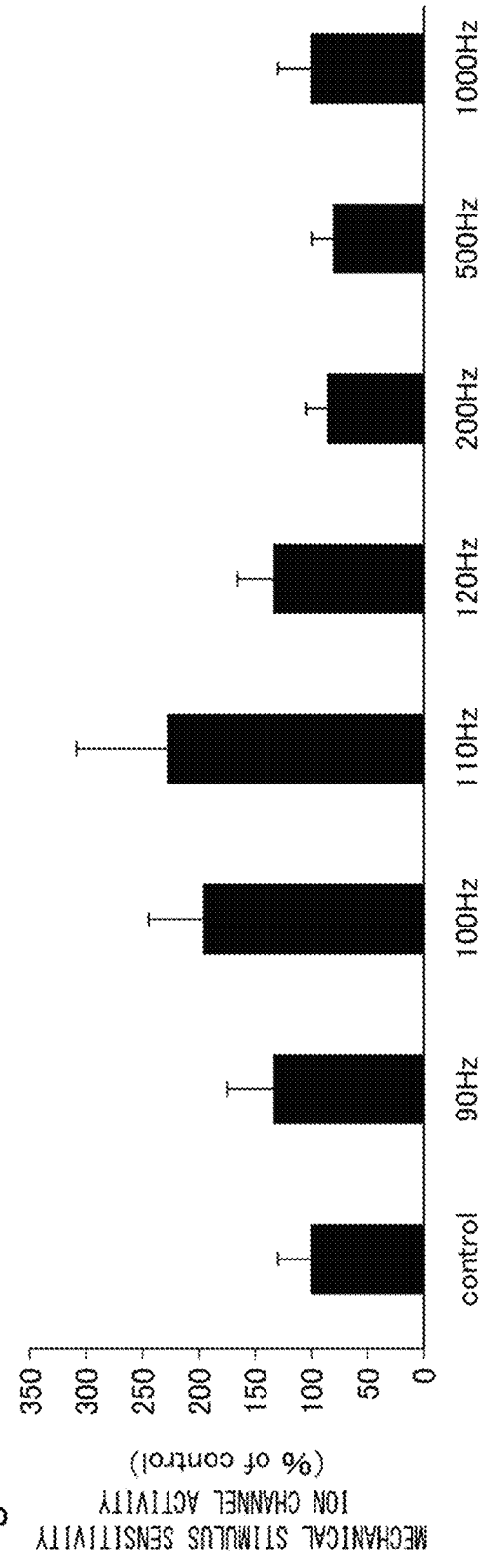
Fig. 7A
Fig. 7B

WITHOUT SOUND STIMULATION

LOW-FREQUENCY SOUND
(CONTINUOUS SOUND 100Hz・85dB)
5 MINUTES

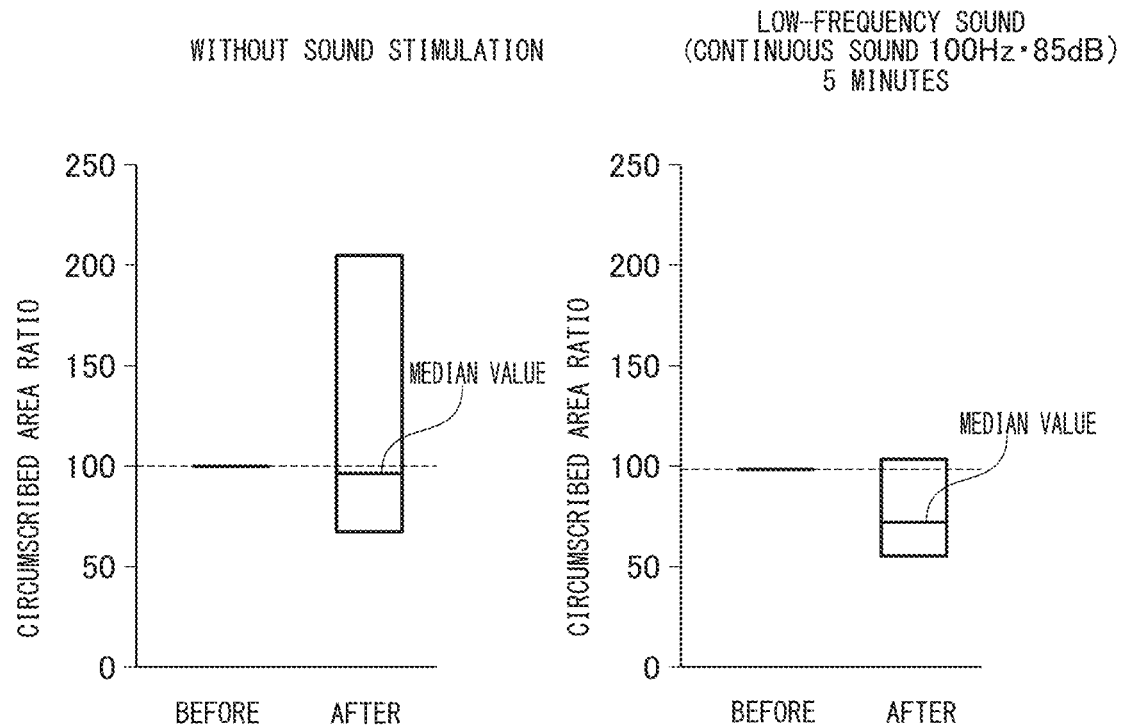

FIG. 16

| | 20Hz | 50Hz | 70Hz | 80Hz | 100Hz | 110Hz | 120Hz | 130Hz | 140Hz | 150Hz |
|---|---|---|---|---|---|---|---|---|---|---|
| 85dB | 67% | 100% | 100% | 100% | 100% | 100% | 100% | 67% | 75% | 0% |

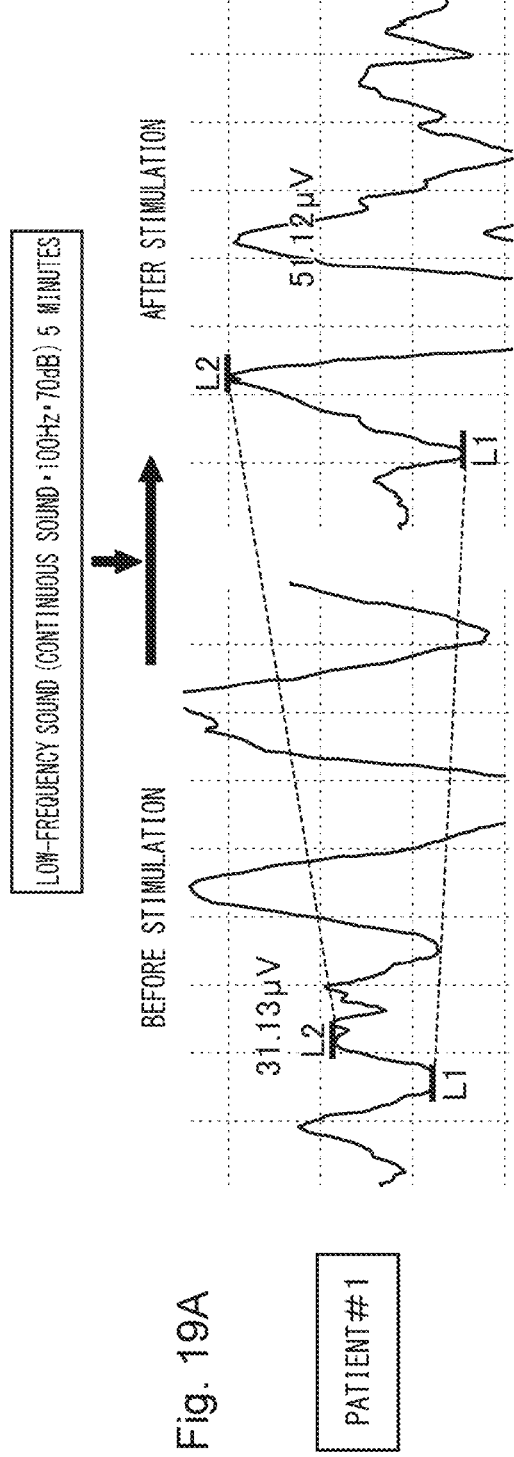
Fig. 19A  PATIENT #1
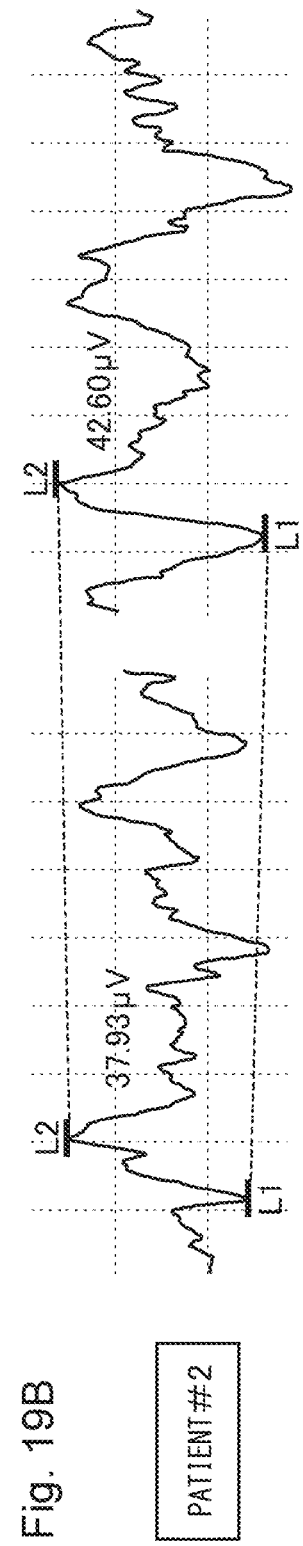
Fig. 19B  PATIENT #2

VESTIBULAR STIMULATION DEVICE, DIZZINESS TREATMENT DEVICE, AND HEALTH PROMOTION DEVICE

CROSS-REFERENCE TO RELATED APPLICATIONS

This application is based upon and claims the benefit of priority from a Japanese Patent Application No. 2018-104637, filed on May 31, 2018, the entire contents of which is incorporated herein by reference.

TECHNICAL FIELD

The present disclosure relates to a technology and an apparatus for improving balance function and motor function of human beings by sound stimulation.

BACKGROUND ART

The main role of the interior ear is to transform vibration into an electrical signal and transmit the electric signal to the nerve or brain. The three semicircular ducts and the vestibule included in the interior ear are known to be related to the function of maintaining the balance of the body (balance function). The vestibule includes the saccule and utricle. Hair cells coupled to the ear stone and otolithic membrane above are located in each of the saccule and utricle. People sense the inclination of the body as the ear stone is inclined in the direction of gravity in association with the inclination of the body.

Non-patent literature 1 discloses a result of adding a solution containing a fluorescence probe (FM1-43) to the interior ear of a mouse to evaluate the function of hair cells in the vestibule and observing a fluorescence signal generated. FM1-43 emits a fluorescence signal when taken up by the cell. When FM1-43 is incorporated into hair cells, intense fluorescence is observed. The observation shows that the transmembrane channel-like (TMC) 1 gene and TMC2 gene for mechanical stimulus sensitivity ion channels are essential for transmission of mechanical signals of the interior ear hair cells and that the balance function is improved as the mechanical stimulus sensitivity ion channels become more active.

[Non Patent Literature 1] Mechanotransduction in mouse inner ear hair cells requires transmembrane channel-like genes. J Clin Invest 121:4796-4809, 2011.

SUMMARY OF INVENTION

Technical Problem

Dizziness begins with a disorder of the balance function. We have focused our attention to the biological effect of sound stimulation. We have conducted various tests and examinations regarding correlation between sound stimulation, motor function, and balance function and have conducted a research to find out sound stimulation suitable for improvement of motor function and balance function.

The disclosure addresses the above-described issue, and a general purpose thereof is to provide a technology in which sound stimulation suitable for improvement of human balance function is used.

Solution to Problem

A vestibule stimulation apparatus according to an embodiment of the present disclosure includes: a setting unit that sets a sound stimulation; and a sound generation unit that generates the sound stimulation thus set. The setting unit sets a sound stimulation having a sound volume level of a value between 70 and 85 decibels and a frequency of a value between 20 and 140 hertz, as a sound stimulation for activating a vestibular function via an ear stone of a subject person. In this disclosure, "ear stone" is used as a term that encompasses ear stone and otolithic membrane.

Another embodiment of the present disclosure relates to a program including computer-implemented modules including: a setting module that sets a sound stimulation having a sound volume level of a value between 70 and 85 decibels and a frequency of a value between 20 and 140 hertz, as a sound stimulation for activating a vestibular function via an ear stone of a subject person; and a sound stimulation generation module that generates the sound stimulation thus set.

Optional combinations of the aforementioned constituting elements, and implementations of the disclosure in the form of methods, apparatuses, systems, recording mediums, and computer programs may also be practiced as additional modes of the present disclosure.

BRIEF DESCRIPTION OF DRAWINGS

FIGS. 6A-6D show that the ear stone is crucial in sensing sound stimulation;

FIGS. 7A-7B show fluorescence levels indicating the activity of hair cells in the utricle observed after a continuous sound stimulation is given at a plurality of frequencies;

FIGS. 13A-13B show ratios of circumscribed area romberg coefficients;

FIG. 16 shows proportions of subject persons showing improvement in the balance function at the respective frequencies;

FIG. 19A and 19B show variations in VEMP of patients of dizziness;

DESCRIPTION OF EMBODIMENTS

Figure 1:
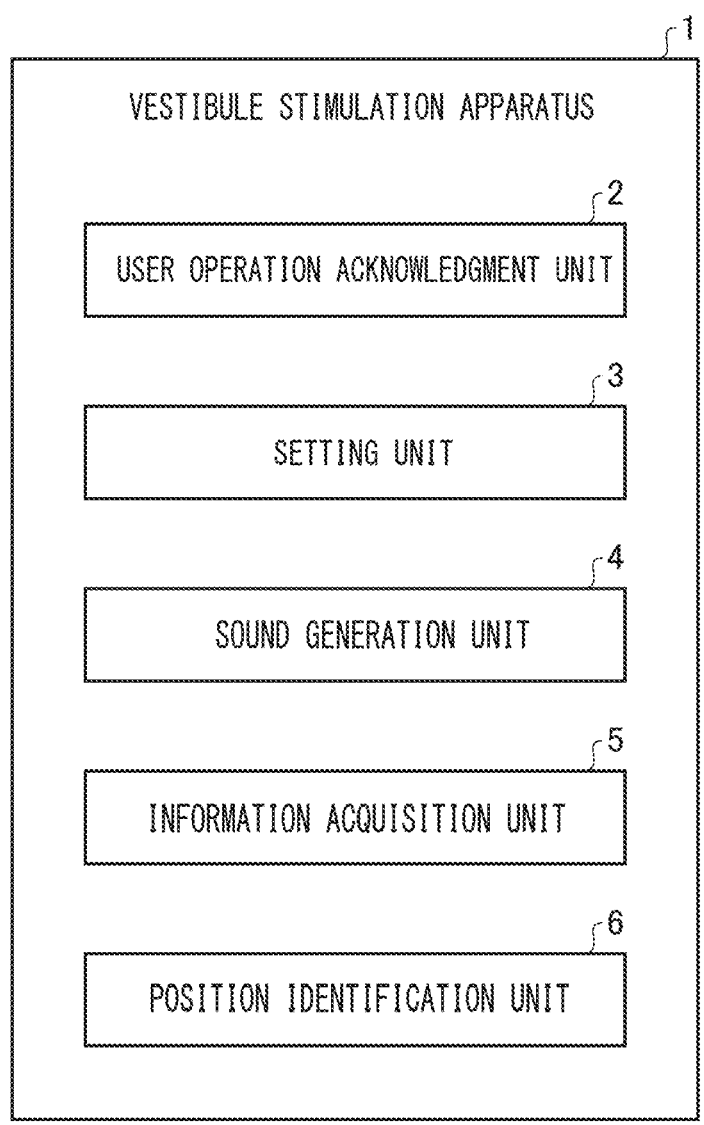
FIG. 1 shows a configuration of a vestibule stimulation apparatus according to an embodiment.

FIG. 1 shows a configuration of a vestibule stimulation apparatus 1 according to an embodiment. The vestibule stimulation apparatus 1 is a sound generation apparatus for generating and outputting sound in a stimulation pattern of a frequency and sound volume that activate the vestibular function of human beings. The sound itself or the sound signal generated in a stimulation pattern of a preset frequency and sound volume may be called "sound stimulation". The vestibule stimulation apparatus 1 includes a user operation acknowledgment unit 2 that acknowledges a user operation to select a sound stimulation, a setting unit that sets a sound stimulation in accordance with a user operation for selection, a sound generation unit 4 that generates and outputs the sound stimulation thus set, an information acquisition unit 5 that acquires information related to the vestibular function of a subject person, and a position identification unit 6 that identifies the position of the subject person relative to the sound generation unit 4. The sound generation unit 4 of the embodiment has a function of outputting pure sound having a specific frequency to the subject person in a temporally continuous manner, but other frequency components may be output simultaneously. The sound generation unit 4 may have a function of a speaker and output sound outside from the vestibule stimulation apparatus 1. Alternatively, the sound generation unit 4 may output sound from a headphone or earphone connected to the vestibule stimulation apparatus 1.

The elements illustrated in FIG. 1 as executing various processes are implemented in hardware such as circuit blocks, memories, or other LSIs and in software such as a program loaded into a memory. Therefore, it will be understood by those skilled in the art that these functional blocks may be implemented in a variety of manners by hardware only, software only, or by a combination of hardware and software.

The vestibule stimulation apparatus 1 of the embodiment outputs a sound stimulation having a sound volume level of a value between 70 and 85 decibel (dB) and a frequency of a value between 20 and 140 hertz (Hz) in order to improve the motor function and balance function of a subject person or promote the anti-aging benefit for the subject person, the detail of which will be described later. The sound volume level means a sound volume level at a position where the subject person is positioned. The sound stimulation is preferably a continuous sound output in a temporarily continuous manner. The sound stimulation is preferably a continuous sound that continues at least for one second or longer, and, more preferably, 30 seconds or longer. In sound stimulation using continuous sound, a sound of a frequency and loudness showing a benefit at the position of the subject person is given continuously.

The vestibule stimulation apparatus 1 may be built in a dizziness treatment apparatus and installed at a medical facility like a hospital. The dizziness treatment apparatus can ameliorate the symptom of dizziness by outputting, to a patient of dizziness, a sound stimulation that activates the vestibular function via the ear stone (hereinafter, "ear stone" includes ear stone and otolithic membrane). The vestibule stimulation apparatus 1 outputs a sound stimulation that stimulates the ear stone and so can be said to be an ear stone stimulation apparatus. The doctor may be allowed to set the sound volume level within a range from 70 to 85 dB and set the frequency within a range from 20 to 140 Hz in accordance with the symptom of the patient or information related to the vestibular function.

Sound stimulation of a sound volume between 70 and 85 dB and a frequency between 20 and 140 Hz comprises sound that people are daily exposed to in terms of sound volume and frequency components and that is highly safe because it meets the environmental criteria. For this reason, the dizziness treatment apparatus provided with the vestibule stimulation apparatus 1 can be used for home therapy under the management of a doctor.

The vestibule stimulation apparatus 1 may be commercially available as health equipment and used for the purpose of improving the motor function and balance function of a healthy person or promoting the anti-aging benefit. It is preferred to form the vestibule stimulation apparatus 1 to be compact so that it can be carried around. It is expected, for example, that an athlete hears the sound stimulation output from the vestibule stimulation apparatus 1 via a headphone before a match. In recent years, prevention of locomotive syndromes is proposed. Prevention and amelioration of locomotive syndromes associated with improvement of the balance function are expected by distributing the vestibule stimulation apparatus 1 as health equipment. Prevention and amelioration of motion disease, which includes travel sickness, and of space sickness, which causes disorder in the vestibular function due to gravitational change, are also expected. It is also expected the apparatus is used to rehabilitation astronauts returning from a stay in the space.

The vestibule stimulation apparatus 1 may be implemented by installing a sound generation application in a mobile terminal apparatus like a smartphone and a tablet. Sound in the range from 70 to 85 dB and the range from 20 to 140 Hz is difficult for ordinary people to hear and, in that sense, can be said to be sound that is not bothering even when it is heard. Therefore, when the user of the mobile terminal apparatus is listening to the music using the music player application, the continuous sound generated by the music generation application may be mixed with the music sound played back. Continuous sound that improves balance function has a low volume and contains relatively lower frequencies than music sound. Therefore, the user can listen to the music without being aware of the continuous sound that is mixed. By mixing continuous sound signals generated by the sound generation application with a musical acoustic signal that is played back, the user can improve the balance function while listening to the music. The sound generation application may be built as a function of the music player application. Alternatively, the sound generation application may be built in other types of applications that output sound such as moving image applications as well as in music player applications.

The vestibule stimulation apparatus 1 may be attached to a chamber that accommodates a subject person and used as a health promotion apparatus. By using the vestibule stimulation apparatus 1 to output a sound stimulation that improves the balance function of the user to the space inside the chamber while the user is in the chamber, the balance function of the user is improved. The health promotion apparatus may be installed at a health club, etc.

We have identified that continuous sound having a sound volume level of a value between 70 and 85 dB and a frequency of a value between 20 and 140 Hz acts upon the ear stone of a subject person and activates the vestibular function via the ear stone. Activation of the vestibular function improves motor function and balance function and promotes anti-aging benefit. A description will now be given of tests and examinations we have conducted.

Figure 2B:
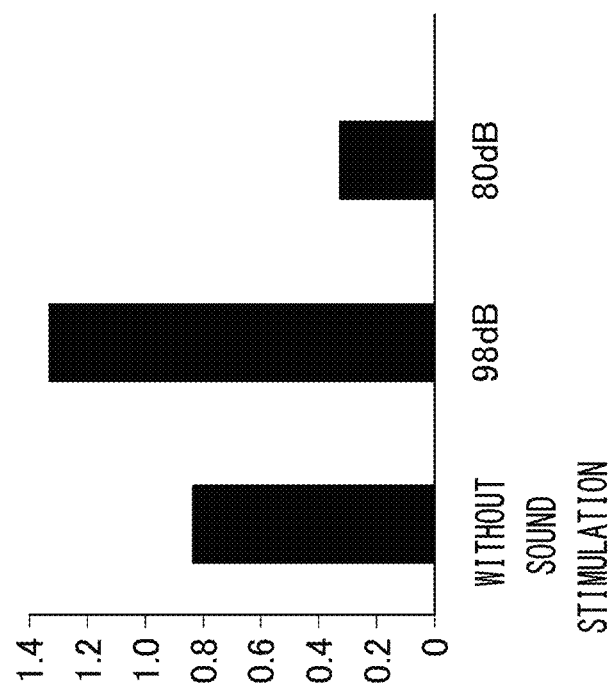
FIGS. 2A-2B show a result of a test on a mouse.
Figure 2A:
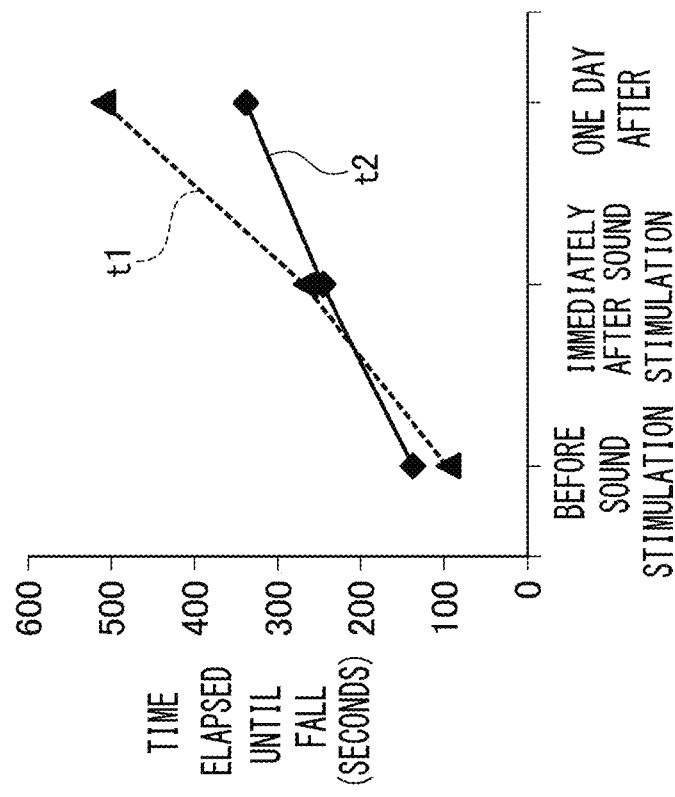

FIG. 2A shows a result of a rotor rod test on mice. A rotor rod test is a test in which a mouse is placed on a rotating rod, the speed is increased gradually, and the time elapsed until the mouse drops is measured. If the motor function and balance function are proper, the time elapsed until the mouse drops from the rod is long. If the motor function and balance function are deteriorated, the time elapsed until the mouse drops from the rod is short.

In the rotor rod test, line t1 denotes a result of measuring the time elapsed until the mouse drops before a sound stimulation is given and after a sound stimulation is given. In this test, a sound stimulation of 75 dB and 100 Hz is given for one hour. Line t1 denotes a variation in the time elapsed until the drop between a point of time before the sound stimulation is given, a point of time immediately after the sound stimulation is given, and one day after the stound stimulation is given. The plots at the respective points of time denote the median value of the time elapsed until the drop of a plurality of mice subject to measurement.

Line t2 denotes a result of measuring the time elapsed until the drop of a mouse not receiving a sound stimulation shown for the purpose of comparison with line t1. In the experiment denoted by line t2, the time elapsed until the drop of a mouse not receiving a sound stimulation is measured at the same points of time (same time intervals) as the mouse receiving a sound stimulation. The plots at the respective points of time denote the median value of the time elapsed until the drop of a plurality of mice subject to measurement.

The rotor rod test shows that the time elapsed until the drop of a mouse receiving a sound stimulation is significantly longer than the time elapsed until the drop of a mouse not receiving a sound simulation. That the time indicated by line t2 grows longer as the rotor rod test is repeated means that the mouse became accustomed to the exercise on the rotor rod. Comparing line t1 and line t2, the motor function and balance function of the mouse are improved by receiving a sound stimulation of a suitable sound volume and frequency.

FIG. 2B shows a result of a balance beam test on mice. In the balance beam test shown in FIG. 2B, the number of times that the mouse slips until the mouse finishes crossing the balance beam is measured. If the motor function and balance function are proper, the number of times of slips will be small. If the motor function and balance function are deteriorated, the number of times of slips will be large.

In this balance beam test, the mice are organized into a group not receiving a sound stimulation, a group receiving a sound stimulation (100 Hz) of 98 dB, and a group receiving a sound stimulation (100 Hz) of 80 dB for the purpose of examining the relationship between the sound volume level and the motor function and balance function. The average value of the numbers of times of slips is measured for each group. The test revealed that the group receiving a sound stimulation of 98 dB showed a poorer record than the group not receiving a sound stimulation. Meanwhile, the group receiving a sound stimulation of 80 dB showed a good record. This means that the motor function and balance function of the mouse were improved when the sound volume level is 80 dB and that, when the sound volume level is 98 dB, on the other hand, the motor function and balance function of the mouse were deteriorated. In other words, the sound volume level of 98 dB was found to induce abnormality in the motor function and balance function of the mouse. A similar test using a sound level of 85 dB (not shown in FIG. 2) also revealed that the sound volume level of 85 dB does not induce abnormality in the motor function and balance function.

We conducted, by using an organ culture system of the inner ear vestibule of a mouse, a "fluorescent probe (FM1-43)" uptake test (see non-patent literature 1) in the mechanical stimulus sensitivity ion channel (TMC1/TMC2) expressed in hair cells, for the purpose of evaluating the direct benefit of sound stimulation for the vestibule, which plays the balance function, and the mechanism thereof. Non-patent literature 1 discloses that the activity of the TMC1/2 ion channel is enhanced, and the balance function, and, ultimately, the vestibule function are improved, when the hair cells of the vestibule take up FM1-43. We gave sound stimulations of a plurality of patterns to the utricle of the mouse and observed a variation in the activity of the ion channel by referring to the variation in the fluorescence intensity resulting from taking up the fluorescent probe.

Figure 3C:
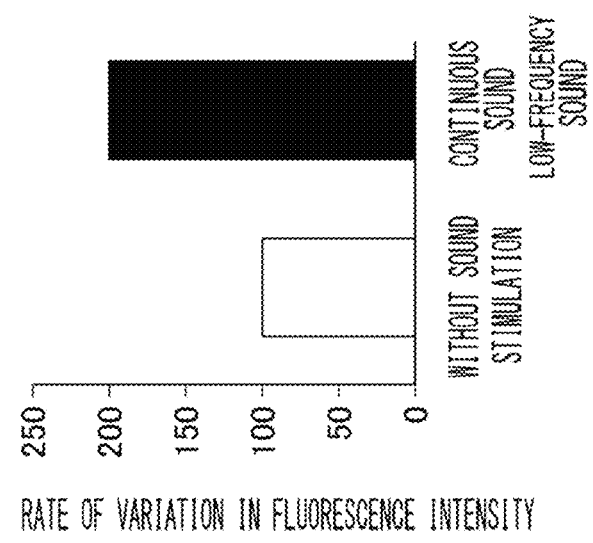
FIGS. 3A-3C show a result of a fluorescent probe uptake test.
Figure 3B:
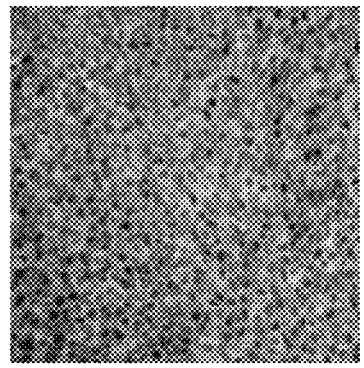
Figure 3A:
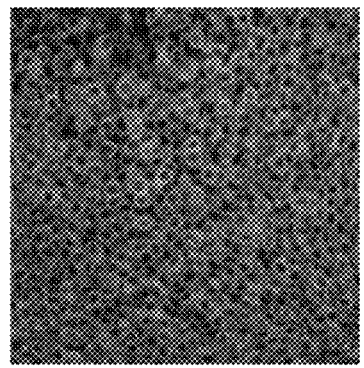

FIG. 3A shows fluorescence in the utricle observed in the absence of a sound stimulation. FIG. 3B shows fluorescence in the utricle observed after a continuous sound of 100 Hz and 85 dB is given for five minutes. FIG. 3C shows a rate of variation in the fluorescence intensity with reference to the fluorescence intensity in the absence of a sound stimulation. The uptake test revealed that the fluorescence intensity is increased by about 100% after a continuous sound stimulation is given. That the fluorescence intensity is increased by giving a continuous sound stimulation means that more of the fluorescent probe is taken up, i.e., that the activity of the TMC1/2 ion channel is enhanced.

Figure 4C:
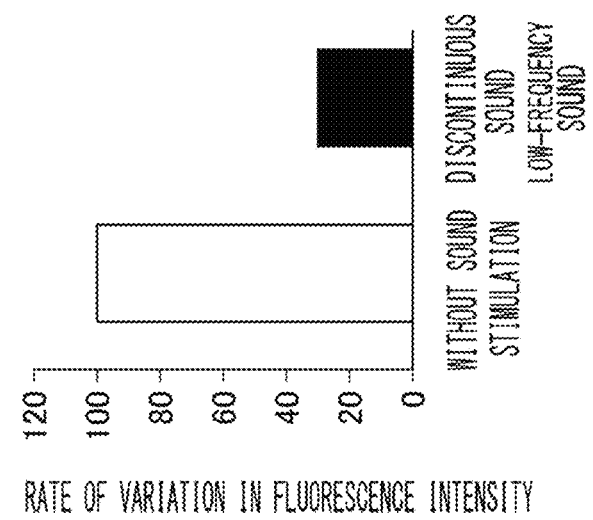
FIGS. 4A-4C show a result of a fluorescent probe uptake test.
Figure 4B:
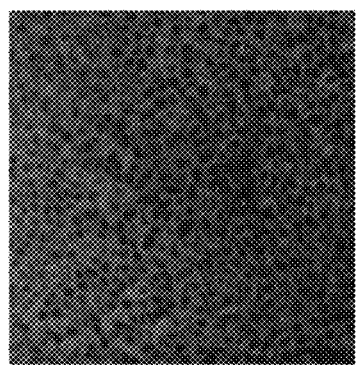
Figure 4A:
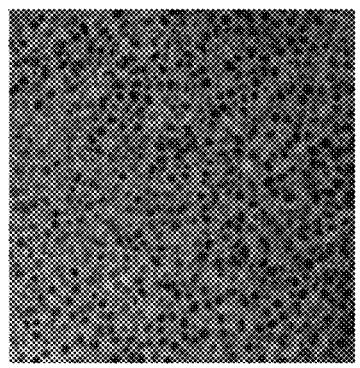

FIG. 4A shows fluorescence in the utricle observed in the absence of a sound stimulation. FIG. 4B shows fluorescence in the utricle observed after a discontinuous sound of 100 Hz and 85 dB is given for five minutes. Discontinuous sound is sound that is not generated in a temporarily continuous manner. The term signifies that generation of sound is temporarily intermittent. The discontinuous sound given in this test is a sound stimulation in which a sound output period when a sound of 100 Hz and 85 dB is output and a non-output period in which sound is output are alternately repeated. The sound output period is configured to last 10 m seconds, and the non-output period is configured to last 600 m seconds so that the non-output period is longer than the sound output period. FIG. 4C shows a rate of variation in the fluorescence intensity with reference to the fluorescence intensity in the absence of a sound stimulation. The uptake test revealed that the fluorescence intensity is decreased by about 70% after a discontinuous sound stimulation is given. That the fluorescence intensity is decreased by giving a discontinuous sound stimulation means that the TMC1/2 ion channel became less active.

The result of the fluorescent probe uptake test relevant to FIGS. 3A-3C and FIGS. 4A-4C reveals that use of a continuous sound makes the vestibular function (balance function) more active and use of a discontinuous sound degrades the vestibular function.

Figure 5A:
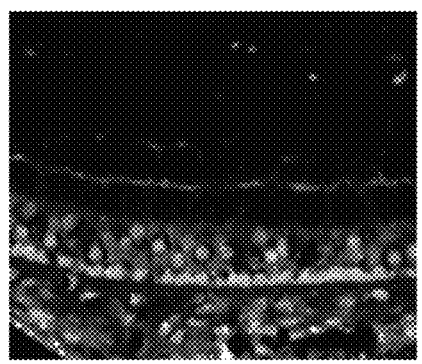
FIGS. 5A-5D show that the ear stone is directly stimulated by sound stimulation.
Figure 5B:
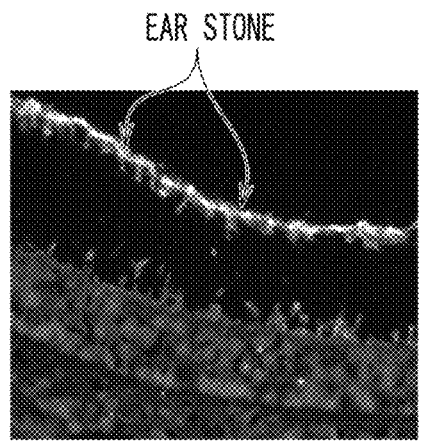

We have conducted an experiment to compare the expression of a heat shock protein 70 in the case where a sound stimulation is given to the ear stone with that of the case where it is not given. FIG. 5A shows a fluorescent state observed when a sound stimulation is not given to the ear stone. In the absence of a sound stimulation, the heat shock protein 70 is not expressed in the ear stone. FIG. 5B shows a fluorescent state observed when a sound stimulation is given to the ear stone. When a sound stimulation is given, the heat shock protein 70 is expressed in the ear stone, and green fluorescence is expressed strongly. It is confirmed from this that sound stimulation directly acts upon the ear stone.

Figure 5C:
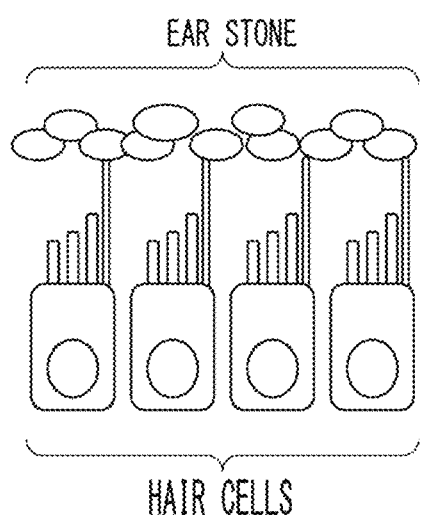
Figure 5D:
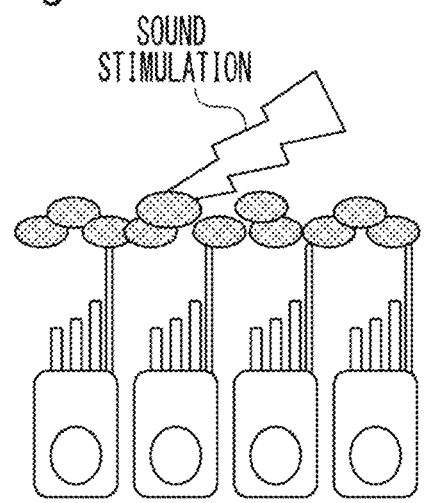

FIGS. 5C and 5D are schematical illustrations of FIGS. 5A and 5B, which show a state in which a a sound stimulation is not given and a state in which a sound stimulation is given, respectively. FIG. 5C schematically shows relative positions of the ear stone and hair cells in the vestibule. The ear stone forms a layer above the hair cells. When a movement in the direction of inclination is applied, the hair cells detect a displacement of the ear stone and transmits a signal to the vestibular nerve. This allows the person to sense the inclination of the body. FIG. 5D is a schematic view showing that a sound stimulation stimulates the ear stone.

We have focused our attention on the role of the ear stone in the vestibular function and conducted an experiment to evaluate whether the vestibular hair cells are activated in response to a sound stimulation, by comparing a state in the presence of the ear stone and a state in the absence of the ear stone. FIG. 6A shows fluorescence in the utricle observed when a sound stimulation is not given in the presence of the ear stone. Because a sound stimulation is not given, the vestibular hair cells are not activated. FIG. 6B shows fluorescence in the utricle observed when a sound stimulation is given in the presence of the ear stone. In this experiment, as in the experiment shown in FIG. 3B, a continuous sound of 100 Hz and 85 dB is given for five minutes, and the fluorescence intensity is increased by about 100% by the continuous sound stimulation. This means that the activity of the TMC1/2 ion channel is enhanced, i.e., the vestibular function is activated.

FIG. 6C shows fluorescence in the utricle observed when a sound stimulation is not given with the ear stone being removed. Since a sound stimulation is not given, the vestibular hair cells are not activated. FIG. 6D shows fluorescence in the utricle observed when a sound stimulation is given with the ear stone being removed. In this experiment, the fluorescence intensity is not increased regardless of the fact that a continuous sound of 100 Hz and 85 dB is given for five minutes. In other words, it was confirmed that the vestibular hair cells are not activated even if a sound stimulation is given with the ear stone being removed.

Based on the experiment result shown in FIG. 6D, we have identified that a continuous sound stimulation of 100 Hz and 85 dB does not act upon the hair cells directly and that such a sound stimulation acts upon the ear stone and, consequently, the vestibular hair cells are activated via the ear stone.

FIGS. 7A-7B show fluorescence levels indicating the activity of hair cells in the utricle observed after a continuous sound stimulation of 85 dB is given at a plurality of frequencies. FIG. 7A shows the fluorescence states at the respective frequencies, and FIG. 7B shows a rate of variation in the fluorescence intensity with reference to the fluorescence intensity in the absence of a sound stimulation. The uptake test confirmed that the benefit of activating the vestibular function is not observed at the frequency of 200 Hz or higher and the benefit of activating the vestibular function via the ear stone is observed at the frequencies lower than 200 Hz.

Based on the knowledge gained by the above tests using the mouse, we have evaluated the balance function of a person by a vestibular evoked myogenic potential (VEMP) test and evaluated the balance function of a person by a gravimetric test. VEMP serves an indicator of the vestibular function including the ear stone function. Improvement in VEMP (increase in the potential) could indicate improvement in the vestibular function including the ear stone function (Hideo Shojaku, Equilibrium Res Vol. 69(3) 168-175, 2010). Since it is publicly known that the ear stone is an aging switch (http://www9.nhk.or.jp/gatten/articles/20161116/index.html), improvement in the vestibular function including the ear stone function can be said to indicate anti-aging benefit as well as improvement in the balance function.

Figure 8:
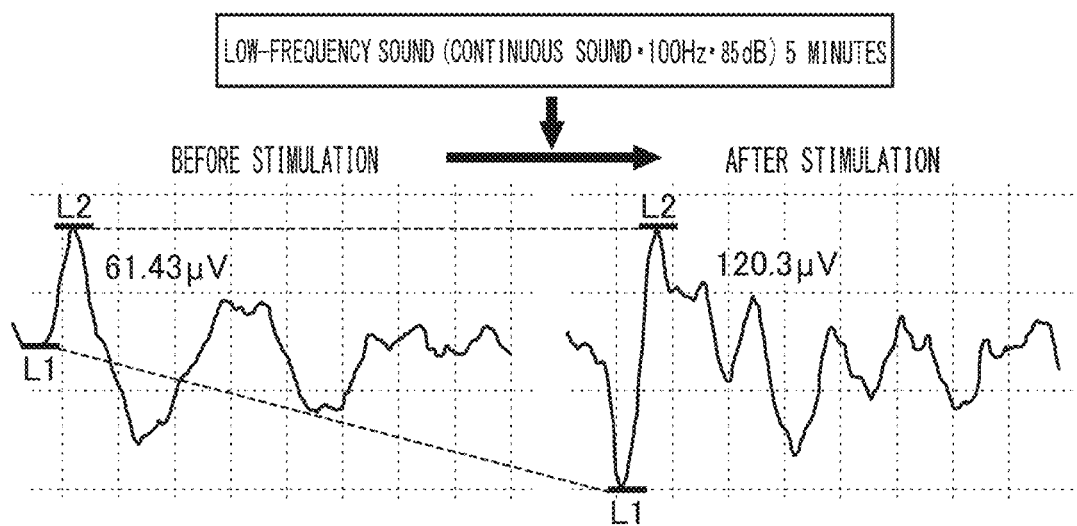
FIG. 8 shows a variation in VEMP of a healthy person.

FIG. 8 shows a variation in VEMP of a healthy person. The test result obtained before a sound stimulation is shown on the left side of FIG. 8, and the test result obtained after a sound stimulation is shown on the right side. The sound stimulation comprises a continuous sound of a sound volume level of 85 dB and a frequency of 100 Hz that lasts for five minutes. The amplitude expansion (L2–L1) in the potential difference in the VEMP test shows improvement in the vestibular function including the ear stone function and, ultimately, improvement in the balance function and promotion of the anti-aging benefit.

Figure 9A:
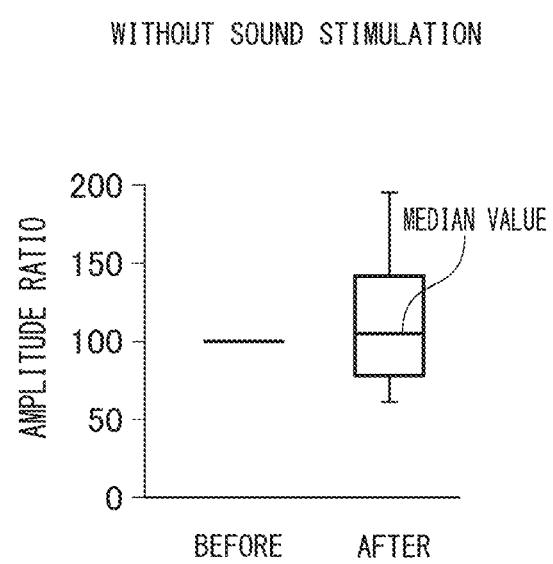
FIGS. 9A-9B shows a VEMP test result.

FIG. 9A shows amplitude ratios for comparison in the VEMP test. The amplitude ratio (=100) shown on the left and labeled "Before" represents a potential difference (L2–L1) observed in the absence of a sound stimulation. The amplitude ratio shown on the right and labeled "After" represents the potential difference in the second test as contrasted with the potential difference in the first test. In the VEMP test shown in FIG. 9A, a sound stimulation is not given in the second test so that a potential difference substantially identical to that of the first test is measured.

Figure 9B:
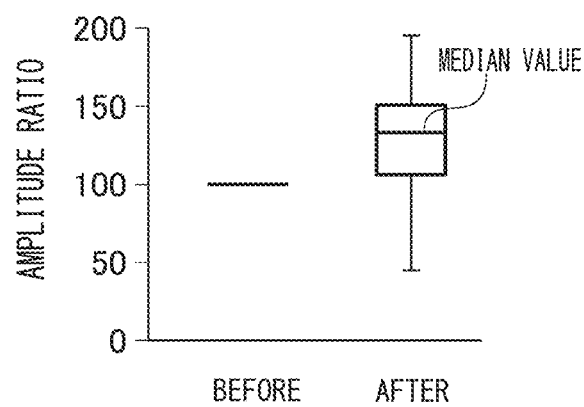

FIG. 9B shows amplitude ratios measured in the VEMP test in which a sound stimulation is given. The amplitude ratio (=100) shown on the left and labeled "Before" represents a potential difference (L2–L1) observed in the absence of a sound stimulation. The amplitude ratio shown on the right and labeled "After" represents the potential difference in the second test as contrasted with the potential difference in the first test. In the VEMP test shown in FIG. 9B, a continuous sound having a sound volume level of 85 dB and a frequency of 100 Hz is given for five minutes in the second test, and the amplitude measured is larger than that of the first test.

The VEMP test result shown in FIGS. 9A-9B confirms that the balance function of a subject person is improved by giving a sound stimulation for activating the vestibular function via the ear stone of the subject person.

Figure 10A:
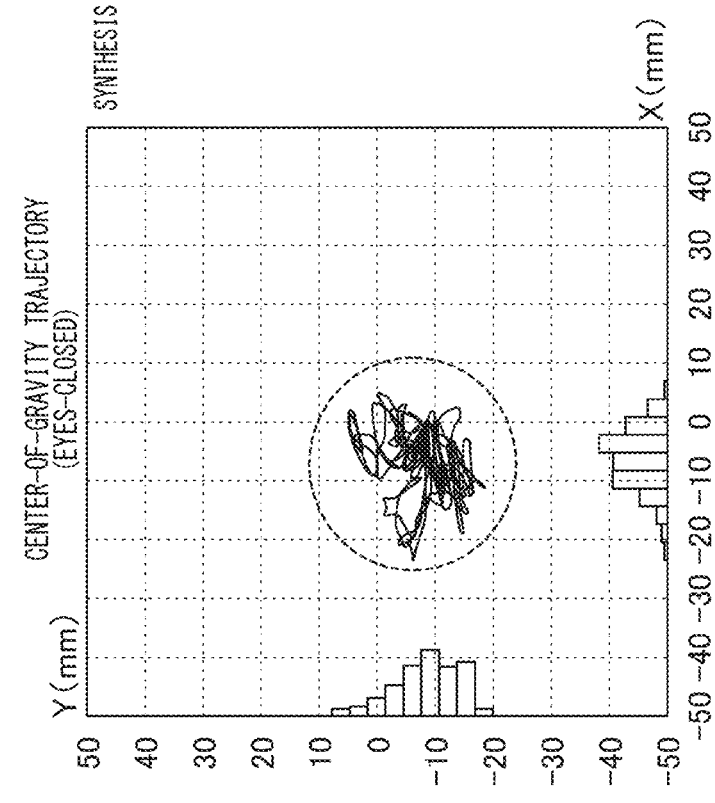
FIGS. 10A-10B show a method of gravimetric test.
Figure 10B:
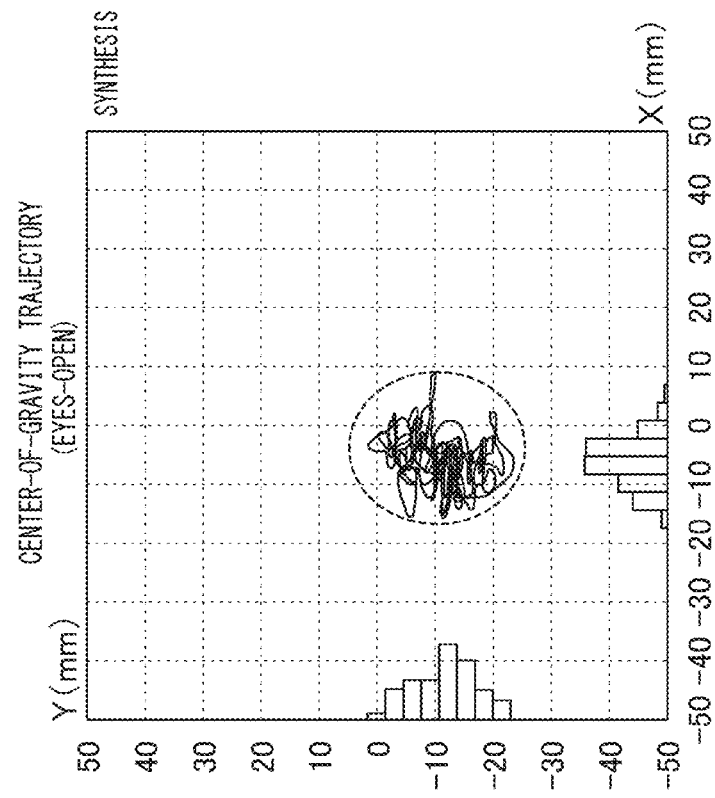

FIGS. 10A-10B show a method of gravimetric test. A gravimetric test is used not only to test the balance function but also to test the motor function. FIG. 10A shows a center-of-gravity trajectory observed when the eyes are open, and FIG. 10B shows a center-of-gravity trajectory observed when the eyes are closed. In a romberg test, which is one of gravimetric tests, a subject person stands erect with feet together. The eyes-open center-of-gravity trajectory over a period of 60 seconds and the eyes-closed center-of-gravity trajectory over a period of 60 seconds are measured. In a romberg test, a romberg coefficient of a trajectory length indicated by (eyes-closed trajectory length/eyes-open trajectory length) and a romberg coefficient of a circumscribed area indicated by (eyes-closed trajectory area (area defined by the trajectory)/eyes-open trajectory area) are used.

Figures 11A, 11B, 11C, 11D:
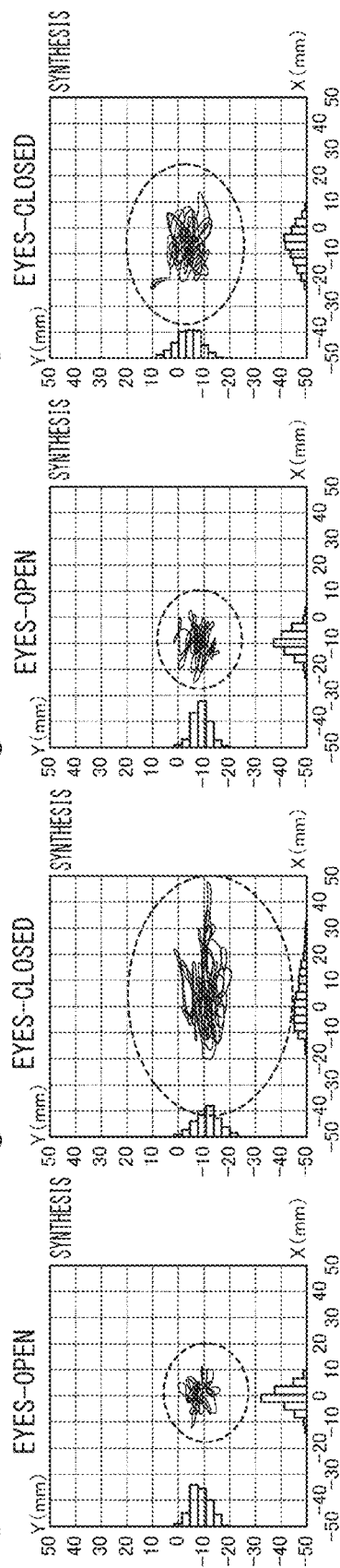
FIGS. 11A-11D show center-of-gravity trajectories.

FIGS. 11A and 11B show center-of-gravity trajectories observed when the eyes are open and when the eyes are closed before a sound stimulation is given to a healthy person. FIGS. 11C and 11D show center-of-gravity trajectories observed when the eyes are open and when the eyes are closed after a sound stimulation is given to a healthy person. The sound stimulation comprises a continuous sound of a sound level of 85 dB and a frequency of 100 Hz that lasts for five minutes. Referring to the eyes-closed center-of-gravity trajectories shown in FIGS. 11B and 11D, the measurement shows that the center-of-gravity sway is smaller after the sound stimulation than before the sound stimulation.

Figure 12A:
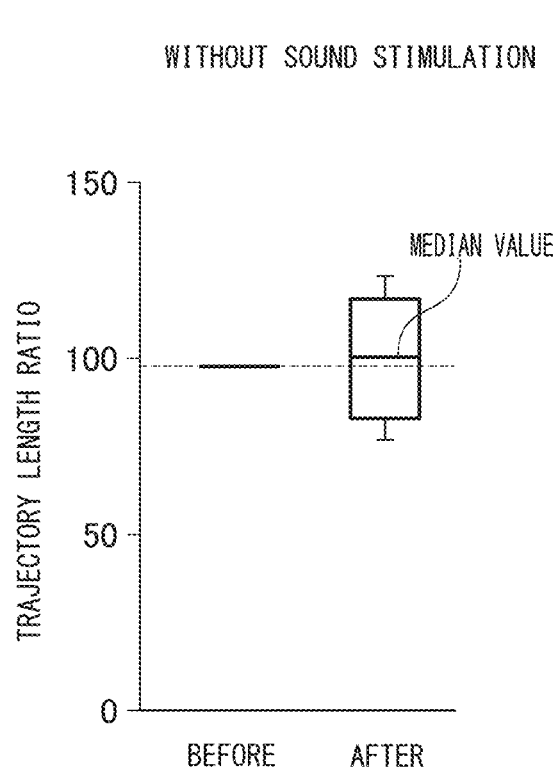
FIGS. 12A-12B show ratios of trajectory length romberg coefficients.

FIG. 12A shows trajectory length romberg coefficients for comparison in a gravimetric test on a healthy person. The trajectory length ratio (=100) shown on the left and labeled "Before" represents a trajectory length romberg coefficient observed in the absence of a sound stimulation. The trajectory length ratio shown on the right and labeled "After" represents the trajectory length romberg coefficient of the second test as contrasted with the trajectory length romberg coefficient of the first test. In the romberg test shown in FIG. 12A, a sound stimulation is not given in the second test so that a trajectory length romberg coefficient substantially identical to that of the first test is calculated.

Figure 12B:
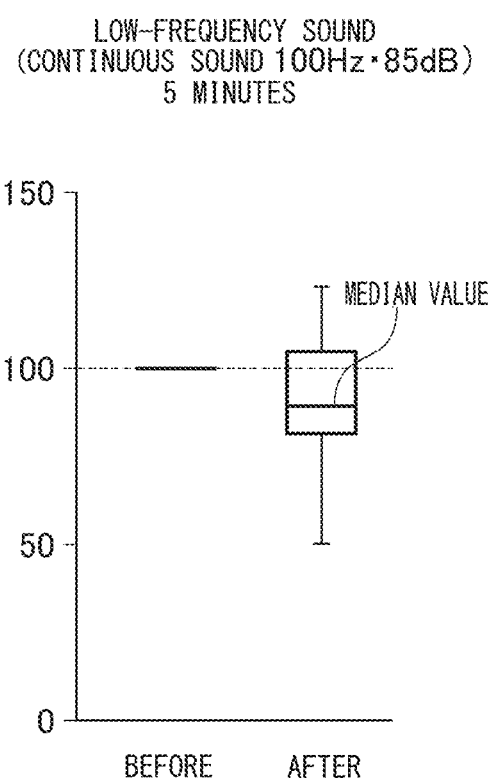

FIG. 12B shows trajectory length romberg coefficients in a gravimetric test on a healthy person in which a sound stimulation is given. The trajectory length ratio (=100) shown on the left and labeled "Before" represents a trajectory length romberg coefficient observed in the absence of a sound stimulation. The trajectory length ratio shown on the right and labeled "After" represents the trajectory length romberg coefficient of the second test as contrasted with the trajectory length romberg coefficient of the first test. In the romberg test shown in FIG. 12B, a continuous sound having a sound volume level of 85 dB and a frequency of 100 Hz is given for five minutes in the second test, and the trajectory length romberg coefficient is smaller than that of the first test. The result confirms that the motor function and balance function of a healthy person are improved by giving a sound stimulation of a suitable pattern to a healthy person.

FIG. 13A shows circumscribed area romberg coefficients for comparison in a gravimetric test on a healthy person. The circumscribed area ratio (=100) shown on the left and labeled "Before" represents a circumscribed area romberg coefficient observed in the absence of a sound stimulation. The circumscribed area ratio shown on the right and labeled "After" represents the circumscribed area romberg coefficient of the second test as contrasted with the circumscribed area romberg coefficient of the first test. In the romberg test shown in FIG. 13A, a sound stimulation is not given in the second test so that a circumscribed area romberg coefficient substantially identical to that of the first test is calculated.

FIG. 13B shows circumscribed area romberg coefficients in a gravimetric test on a healthy person in which a sound stimulation is given. The circumscribed area ratio (=100) shown on the left and labeled "Before" represents a circumscribed area romberg coefficient observed in the absence of a sound stimulation. The circumscribed area ratio shown on the right and labeled "After" represents the circumscribed area romberg coefficient of the second test as contrasted with the circumscribed area romberg coefficient of the first test. In the romberg test shown in FIG. 13B, a continuous sound having a sound volume level of 85 dB and a frequency of 100 Hz is given for five minutes in the second test, and the circumscribed area romberg coefficient is smaller than that of the first test. The result confirms that the motor function and balance function of a healthy person are improved by giving a suitable sound stimulation to the healthy person.

FIGS. 11A-13B show results of gravimetric tests using eyes-open and eyes-closed center-or-gravity trajectories. The tests shown in FIGS. 14-16 examine the benefit of sound stimulation for the vestibular function of a person affected with motion sickness. In this test, the center-of-gravity trajectory of a subject person is measured first. The same subject person is caused to sit on a chair, and the center-of-gravity trajectory of the subject person is measured after rotating the chair 12 times for one minute.

Figure 14:
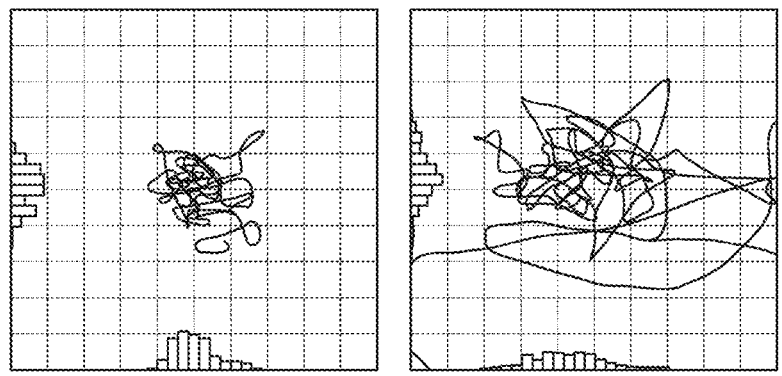
FIG. 14 shows a center-of-gravity trajectory observed before a rotational stimulation and a center-of-gravity trajectory observed after the rotational stimulation.

FIG. 14 shows a center-of-gravity trajectory observed before a rotational stimulation and a center-of-gravity trajectory observed after the rotational stimulation. In the test shown in FIG. 14, a sound stimulation is not given to the subject person. In this case, the fluctuation of center-of-gravity given by (trajectory area observed after rotational stimulation/trajectory area observed before rotational stimulation) was 16.0.

Figures 15A, 15B:
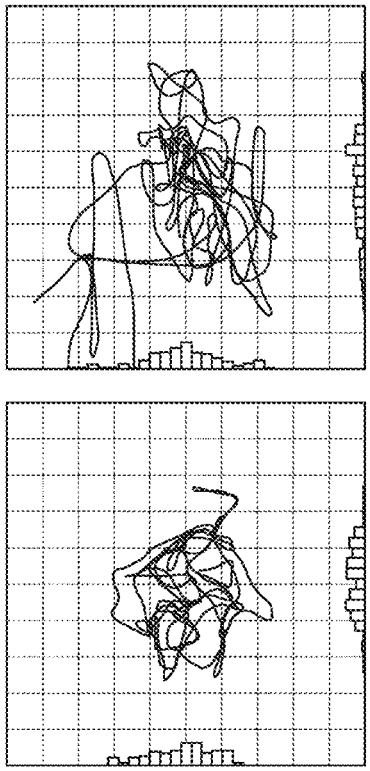
FIGS. 15A-15B show a center-of-gravity trajectory observed before a rotational stimulation and a center-of-gravity trajectory observed after the rotational stimulation.

A test result obtained when a sound stimulation was given to a subject person while the chair was being rotated will be shown. FIG. 15A shows a center-of-gravity trajectory observed before a rotational stimulation and a center-of-gravity trajectory after the rotational stimulation. In the test shown in FIG. 15A, a sound stimulation of 70 dB and 100 Hz was given to a subject person for one minute while the chair was being rotated. The fluctuation of center-of-gravity in this case is 3.1. It was confirmed that the vestibular function is activated and the balance function is significantly improved as compared with the fluctuation in the case shown in FIG. 14 in which a sound stimulation is not given.

FIG. 15B shows a center-of-gravity trajectory observed before a rotational stimulation and a center-of-gravity trajectory observed after the rotational stimulation. In the test shown in FIG. 15B, a sound stimulation of 85 dB and 100 Hz was given to a subject person for one minute while the chair is being rotated. The fluctuation of center-of-gravity in this case is 1.3. It was confirmed that the vestibular function is activated and the balance function is significantly improved as compared with the fluctuation in the case shown in FIG. 14 in which a sound stimulation is not given.

Based on the above test result, we have conducted a gravimetric test using a chair on a plurality of subject persons at different frequencies and measured a degree of improvement in the balance function of the subject persons. FIG. 16 shows proportions of subject persons showing improvement in the balance function at the respective frequencies. In this test, the sound volume level of a sound stimulation given while the chair is being rotated is fixed at 85 dB, and the proportion of subject persons showing improvement in the balance function is measured at a plurality of frequencies from 20 Hz to 150 Hz. It was confirmed that the benefit of improvement in the balance function was confirmed in 67% of the subject persons at 20 Hz, 100% at 50-120 Hz, 67% at 130 Hz, and 75% at 140 Hz. Meanwhile, improvement in the balance function was not confirmed at 150 Hz.

Thus, tests conducted on persons confirmed that a sound stimulation having a sound volume level of 85 dB and a frequency in a range from 20 Hz and 140 Hz provides the benefit of activating the vestibular function via the ear stone of the subject person. A similar benefit of improvement was also confirmed in the case the sound volume level is set to 70 dB as in the case of 85 dB. The results shown in FIGS. 14-16 confirmed that the sound stimulation in the above range may also stimulate the semicircular canal.

Recently, it has been reported that lack of stimulation of the ear stone due to a seated position maintained for a long period of time poses a risk of aging. In reality, attempts have been made, in some Japanese companies as well as in Australian schools, to stimulate the ear stone and preventing aging by changing from a seated position to a standing position by periodical (e.g., every one hour) elevations of the desk.

Figure 17:
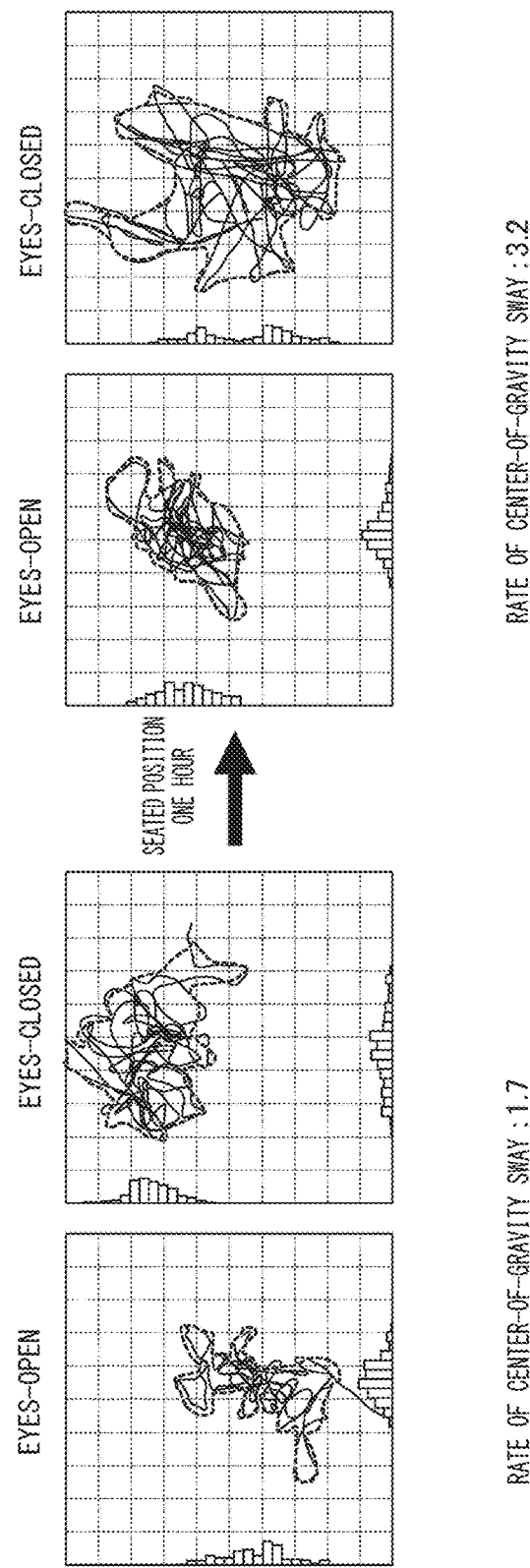
FIG. 17 shows how the fluctuation of center-of-gravity is changed when the seated position is maintained.
Figure 18:
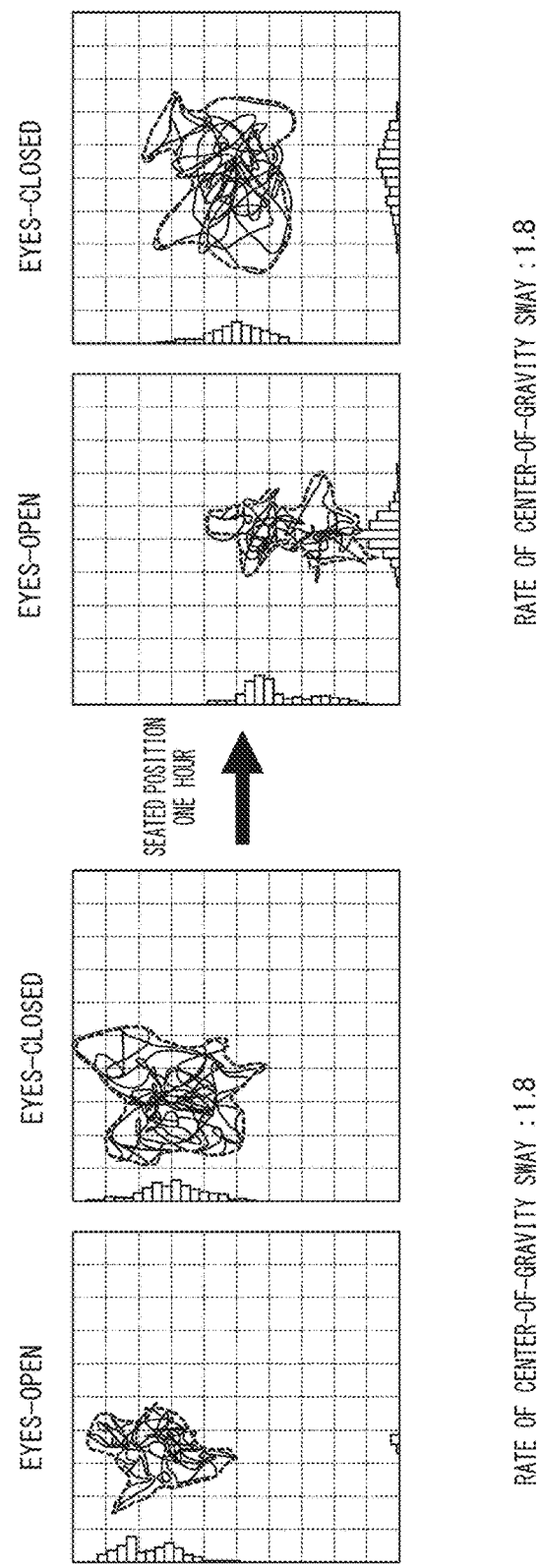
FIG. 18 shows how the fluctuation of center-of-gravity is changed when the seated position is maintained.

The tests shown in FIGS. 17-18 examine the benefit of sound stimulation exerted on the vestibular function when a seated position is maintained. In these tests, the fluctuation of center-of-gravity (=eyes-closed trajectory area/eyes-open trajectory area) was first measured with the eyes of the subject person closed and with the eyes open, and then the fluctuation of center-of-gravity was measured with the eyes closed and with the eyes open after the subject person is seated in a chair for one hour. The subject person remained still in the seated position for one hour.

FIG. 17 shows how the fluctuation of center-of-gravity is changed when the seated position is maintained. In the test shown in FIG. 17, a sound stimulation is not given to the subject person in the seated position. The fluctuation of center-of-gravity observed before the subject person takes the seated position was 1.7, and the fluctuation of center-of-gravity observed after the subject person maintained the seated position for one hour was 3.2. This test confirmed that the ear stone is not stimulated because the subject person remained seated still in the char for one hour and that a disorder is caused in the balance function.

FIG. 18 shows how the fluctuation of center-of-gravity is changed when the seated position is maintained. In the test shown in FIG. 18, a continuous sound stimulation of 85 dB and 100 Hz was given three times to a subject person maintaining a seated position for one hour. Specifically, the sound stimulation was given for 5 minutes immediately after the seated position is started, for five minutes after 25 minutes, and for five minutes after 55 minutes. As illustrated, the fluctuation of center-of-gravity observed before the subject person takes the seated position was 1.8, and the fluctuation of center-of-gravity observed after the subject person maintained the seated position for one hour was also 1.8. This test confirmed that a disorder in the balance function is not caused as a result of stimulating the ear stone by giving a continuous sound stimulation of five minutes three times while the subject person remain seated in the chair for one hour.

The tests above confirmed that the balance function is deteriorated if the seated position is maintained and that the deterioration of the balance function is ameliorated by giving a continuous sound stimulation while the seated position is maintained.

FIGS. 19A and 19B show variations in VEMP of patients of dizziness. FIG. 19A shows a variation in VEMP of a patient in his(her) 80's suffering from serious dizziness, and FIG. 19B shows a variation in VEMP of a patient in his(her) 50's suffering from mild dizziness. In FIGS. 19A and 19B, the test result obtained before a sound stimulation is shown on the left, and the test result obtained after the sound stimulation is shown on the right. The sound stimulation comprises a continuous sound of a sound level of 70 dB and a frequency of 100 Hz that lasts for five minutes. The amplitude of the potential difference (L2–L1) in the VEMP test is expanded. The amplitude expansion shows that there is improvement in the vestibular function of the patients of dizziness regardless of the age and the seriousness of symptom of the patient of dizziness.

In the VEMP test shown in FIG. 8, a continuous sound stimulation of a sound level of 85 dB and a frequency of 100 Hz that lasts five minutes is given to a healthy person. In the VEMP test shown in FIG. 19, a continuous sound stimulation of a sound level of 70 dB and a frequency of 100 Hz that lasts five minutes is given to a patient of dizziness. In either case, results showing improvement in the balance function were obtained. Described above is an objective evaluation result. In practice, a lot of patients of dizziness reported that the symptom is ameliorated.

The tests described above confirmed that a continuous sound having a sound volume level of a between 70 and 85 dB and a frequency of a value between 20 and 140 Hz is a sound stimulation that stimulates the ear stone of a subject person and is effective to remedy or improve the balance function by activating the vestibular function via the ear stone.

Referring back to FIG. 1, the setting unit 3 in the vestibule stimulation apparatus 1 sets a sound stimulation having a sound volume level of a between 70 and 85 dB and a frequency of a value between 20 and 140 Hz, and the sound generation unit 4 generates the sound stimulation thus set and outputs it to the subject person.

When the sound stimulation is output, the information acquisition unit 5 acquires information related to the vestibular function of the subject person. The information related to the vestibular function includes status information representing the status of the current vestibular function of the subject person. The status information may be information that makes it possible to estimate whether the current vestibular function is proper or degraded. As mentioned above, the test confirmed that the balance function is degraded when the seated position of the subject person is maintained for a long period of time. Therefore, the information acquisition unit 5 may acquire a duration in which the seated position of the subject person is maintained, as the information indicating the vestibular function. The information acquisition unit 5 may, for example, acquire a camera image capturing the subject person and acquire the duration of the seated position by performing image analysis. Alternatively, the information acquisition unit 5 may acquire the duration of the seated position of the subject person by referring to the value detected by a load sensor provided on the seat of the chair. When an objective is to improve the balance function of a subject person doing desk work, the camera may be installed in advance to capture the desk, and the information acquisition unit 5 may be supplied with an image from the camera. The duration of the seated position may be measured by a further device and supplied to the information acquisition unit 5.

The setting unit 3 sets at least one of the sound volume level or frequency of the sound stimulation in accordance with the information related to the vestibular function acquired by the information acquisition unit 5. For example, when the duration of the seated position of the subject person is provided from the information acquisition unit 5, the setting unit 3 may not generate a sound stimulation if the duration of the seated position is within a predetermined time (e.g., 30 minutes) and generate a sound stimulation if the duration exceeds the predetermined time, setting the sound volume level in a range 70-85 dB. The setting unit 3 may set at least one of the sound volume level or frequency of the sound stimulation in accordance with the duration of the seated position. Thus, it is preferred that the setting unit 3 set a sound stimulation suited to the status of the vestibular function of the subject person in accordance with the information related to the vestibular function of the subject person.

In another example, the information acquisition unit 5 may acquire information related to the movement of the head of the subject person, as the information related to the vestibular function. The information acquisition unit 5 may acquire the degree of movement of the head by, for example, acquiring a camera image capturing the subject person and performing image analysis. The information acquisition unit 5 may acquire the information related to the movement of the head measured by a further device from the further device. When the head is still, the ear stone is not stimulated, and the balance function tends to be degraded. Accordingly, the information acquisition unit 5 may acquire the information related to the movement of the head and provide the information to the setting unit 3 as the information related to the current vestibular function. The setting unit 3 may set at least one of the sound volume level or frequency of a sound stimulation in accordance with the information related to the movement of the head of the subject person. If the amount of movement of the head is relatively great, for example, the sound volume level of the sound stimulation may be decreased within the range 70-85 dB, and, if the amount of movement of the head is relatively small, the sound volume level of the sound stimulation may be increased within the range 70-85 dB. The movement of the head may be acquired by a motion sensor, acceleration sensor, or the like. The information acquisition unit 5 may acquire the movement of the center of gravity of the subject person in a seated position, as the information related to the vestibular function.

The information acquisition unit 5 may acquire the movement of the eyes of the subject person, the change in the facial expression of the subject, etc. as the status information representing the status of the current vestibular function. The information acquisition unit 5 may acquire attribute information such as age, sex, BMI of the subject person and provide the attribute information to the setting unit 3, and the setting unit 3 may use the attribute information as a compensation coefficient for the sound volume level and frequency that are set.

The position identification unit 6 identifies the position of the subject person relative to the sound generation unit 4, and the setting unit 3 determines the sound volume level output from the sound generation unit 4 in accordance with the position of the subject person. More specifically, the setting unit 3 determines the sound volume level output from the sound generation unit 4 such that the sound volume level at the position where the subject person is positioned is of a value between 70 and 85 dB. The position identification unit 6 may identify the position of the subject person by, for example, referring to a camera image capturing the subject person. The setting unit 3 derives a distance between the sound generation unit 4 and the subject person and determines the sound volume level output from the sound generation unit 4, allowing for the distance attenuation of the sound. If the sound volume level for the subject person is set to be 75 dB, for example, the output level of the sound generation unit 4 may be determined to be a sound volume level derived from adding the distance attenuation component to 75 dB.

We have measured the fluctuation of center-of-gravity observed before and after a rotational stimulation when a sound stimulation is given to the subject person from right, from left, and from behind. We obtained a result showing that the fluctuation of center-of-gravity is smallest when the sound stimulation is given from behind. We have learned from this result that it is most effective for improvement of the balance function to give a sound stimulation uniformly to the left and right ear stones. This knowledge may be utilized to cause the setting unit 3 to control the output of the sound generation unit 4 such that the sound volume levels for stimulating the left and right ear stones of the subject person are substantially equal. For example, the sound generation unit 4 may include the first sound generation unit that generates a sound stimulation toward one of the ears of the subject person and the second sound generation unit that generates a sound stimulation toward the other ear of the subject person. The setting unit 3 may control the output of the first sound generation unit and the output of the second sound generation unit independently such that the sound volume levels for stimulating the left and right ear stones of the subject person are substantially equal. When an objective is to improve the balance function of a subject person doing desk work, for example, the first sound generation unit and the second generation unit may be provided at positions that sandwich a subject person seated in a chair from left and from right. The setting unit 3 may set the output level of the first sound generation unit and the output level of the second sound generation unit such that the sound volume levels for stimulating the left and right ear stones of the subject person are substantially equal.

Figure 20:
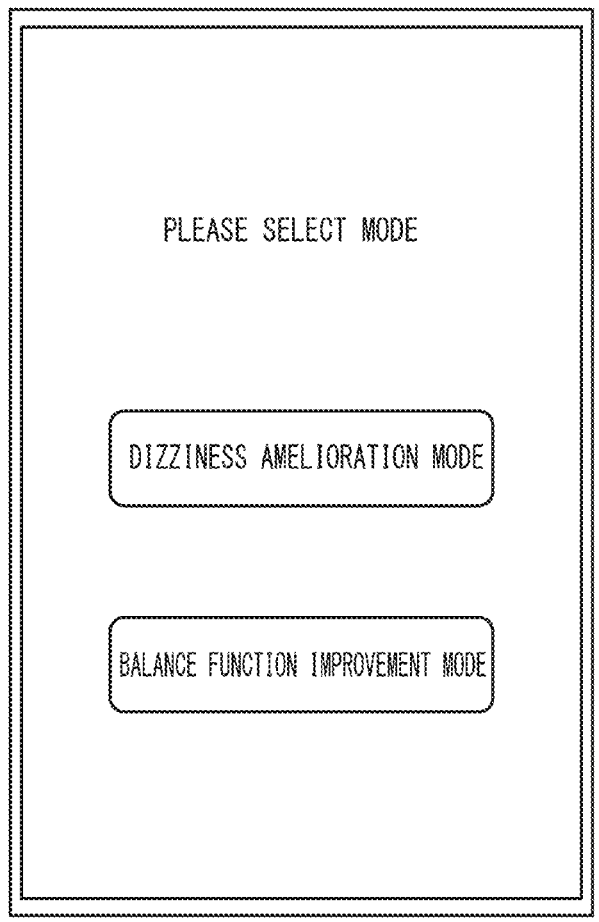
FIG. 20 shows an exemplary screen displayed in the vestibule stimulation apparatus.

When the setting unit 3 sets a sound stimulation, the user operation acknowledgment unit 2 may acknowledge a user operation to select a sound stimulation for improving the motor function, improving the balance function, or promoting the anti-aging benefit. FIG. 20 shows an exemplary screen displayed in the vestibule stimulation apparatus 1. For example, the vestibule stimulation apparatus 1 may be a mobile terminal apparatus such as a smartphone in which a sound generation application is installed. When the sound stimulation is set, a plurality of types of modes for setting a sound stimulation are prepared in the sound generation application. In this example, "dizziness amelioration mode" for patients of dizziness and "balance function improvement mode" for healthy persons are displayed as being selectable, but other modes may be prepared.

It is preferred to set the sound volume level to be smaller in the "dizziness amelioration mode" than in the "balance function improvement mode". For example, a continuous sound having a sound volume level of 70 dB and a frequency of 100 Hz that lasts five minutes is registered as the stound stimulation in the "dizziness amelioration mode", and a continuous sound having a sound volume level of 85 dB and a frequency of 100 Hz that lasts five minutes is registered as the sound stimulation in the "balance function improvement mode". The setting unit 3 has a function capable of setting a sound stimulation suited to the plurality of types of modes.

More specifically, when the user selects one of the plurality of types of modes, the user operation acknowledgment unit 2 acknowledges a mode selection operation from the user, and the setting unit 3 sets a sound stimulation suited to the mode selection operation acknowledged. The user need not set a parameter such as a sound volume level and a frequency individually and can set a sound stimulation merely by using a mode button. Thus, the usability of the vestibule stimulation apparatus 1 is improved.

The sound generation unit 4 may include, in consideration of the safety of the user, a function of limiting the time for which the sound is generated within a prescribed time frame to be a predetermined period of time or shorter. For example, the sound generation unit 4 may limit the time for which the user can hear the sound within a time frame of 24 hours to be 30 minutes or shorter. For this purpose, the vestibule stimulation apparatus 1 may have a function of identifying the user by biometric authentication, and the sound generation unit 4 may count, for each user, the time for which the sound is generated within a prescribed time frame and prohibit generation of sound beyond a predetermined period of time.

In the case the mobile terminal apparatus has a function of playing back music data, the sound generation unit 4 may generate a preset sound stimulation while music data is being played back. This lets the user derive the benefit of improving the balance function while listening to the music.

Further, by mounting the vestibule stimulation apparatus 1 in various transportation means including automobiles, trucks, ships, airplanes, rockets, and spaceships and generating a sound stimulation of a continuous sound having a sound volume level of a value between 70 and 85 decibels and a frequency of a value between 20 and 140 hertz, improvement in balance function of healthy and aged persons, reduction of traffic accidents due to improvement in balance function, relief of motion sickness and space sickness, etc. are expected. Further, by installing the vestibule stimulation apparatus 1 in residences and factories, improvement in balance function, reduction of slip and fall accidents due to improvement in balance function, and creation of healthful residences (smart houses) and healthful working places (smart factories) are expected.

Further, as described above, by using the information acquisition unit 5 to acquire the duration of the seated position of the subject person and the information related to the movement of the head, and by using the setting unit 3 to set at least one of the sound volume level or frequency of the sound stimulation in accordance with the acquired information, the deterioration of the balance function is properly inhibited in accordance with the situation of the subject person. By installing a camera at a position where the camera can capture the place such as a school, residence, working place, etc. where the subject person takes a seated position and using the information acquisition unit 5 to acquire status information representing the status of the current vestibular function, anti-aging benefit from stimulation of the ear stone is also expected.

Figure 21:
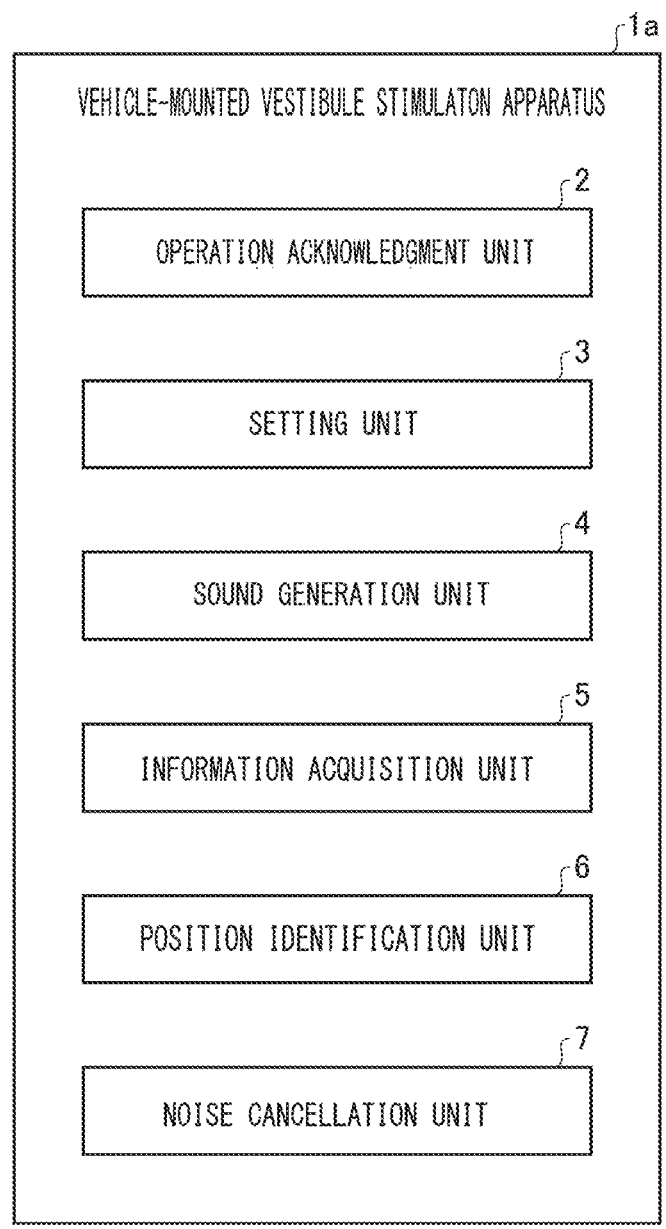
FIG. 21 shows a configuration of a vehicle-mounted vestibule stimulation apparatus according to an example.

FIG. 21 shows a configuration of a vehicle-mounted vestibule stimulation apparatus 1a according to an example. The vehicle-mounted vestibule stimulation apparatus 1a is produced by adding a noise cancellation unit 7 to the configuration of the vestibule stimulation apparatus 1 in order to cause the vestibule stimulation apparatus 1 shown in FIG. 1 to function as an apparatus for use in a vehicle. The vehicle-mounted vestibule stimulation apparatus 1a is mounted on a vehicle like an automobile and has a function of preventing or inhibiting travel sickness of a passenger. Alternatively, the apparatus may be mounted on other transportation means (e.g., ships, airplanes, rockets, spaceships).

The position identification unit 6 in the vehicle-mounted vestibule stimulation apparatus 1a detects whether a passenger is present inside the vehicle. The position identification unit 6 may detect whether a passenger is present or not by acquiring an image from a camera for capturing the scene in the vehicle interior and subjecting the image thus taken to image analysis. When a passenger is detected, the position identification unit 6 identifies the position of the passenger in the vehicle interior.

In the vehicle-mounted vestibule stimulation apparatus 1a, the setting unit 3 sets a sound stimulation of a continuous sound having a sound volume level of a value between 70 and 85 decibels and a frequency of a value between 20 and 140 hertz and configured to prevent or inhibit motion sickness including travel sickness, and the sound generation unit 4 generates the sound stimulation thus set and outputs the generated stimulation inside the vehicle. It is preferred that the sound generation unit 4 have a directional speaker and output the sound stimulation toward the position of the passenger identified by the position identification unit 6. By outputting the sound stimulation toward the passenger, travel sickness of the passenger is effectively prevented.

When the user operation acknowledgment unit 2 acknowledges an on-operation to generate a sound stimulation from a passenger, the sound generation unit 4 may generate the sound stimulation set by the setting unit 3. The sound generation unit 4 may generate a sound stimulation automatically in accordance with the running condition of the vehicle, and, more specifically, when the vehicle is in a running condition in which the vehicle is rocked heavily and travel sickness occurs easily. Whether the vehicle is in a running condition in which travel sickness occurs easily may be judged by the information acquisition unit 5 based on the value detected by a vehicle-mounted acceleration sensor.

Balance function is directly linked to the driving technique, which will be appreciated by seeing drunk driving and meandering driving of aged people. Causing the sound generation unit 4 to output a sound stimulation toward the driver is expected to improve the driving technique by improving the balance function of the driver. Meanwhile, the output toward a passenger is expected to reduce carsickness.

The noise cancellation unit 7 has a role of canceling the noise inside the vehicle. The noise cancellation unit 7 detects the noise generated inside the vehicle and generates a sound having a phase opposite to that of the noise to cancel the noise. By canceling the noise, the benefit of the sound stimulation output by the sound generation unit 4 is enhanced. An acoustic insulation member or a silencing apparatus may be provided inside the vehicle to cancel the noise.

Given above is a description of the present disclosure based on an exemplary embodiment. The embodiment is intended to be illustrative only and it will be obvious to those skilled in the art that various modifications to constituting elements and processes could be developed and that such modifications are also within the scope of the present invention.

A summary of an embodiment of the present disclosure is given below. A vestibule stimulation apparatus according to one embodiment of the present disclosure includes: a setting unit that sets a sound stimulation; and a sound generation unit that generates the sound stimulation thus set. The setting unit sets a sound stimulation having a sound volume level of a value between 70 and 85 decibels and a frequency of a value between 20 and 140 hertz, as a sound stimulation for activating a vestibular function via an ear stone of a subject person.

The vestibule stimulation apparatus may further include: an information acquisition unit that acquires information related to the vestibular function of the subject person. The setting unit may set at least one of the sound volume level or a frequency of the sound stimulation in accordance with the information related to the vestibular function thus acquired. The information acquisition unit may acquire status information representing a status of a current vestibular function. The information acquisition unit may acquire a duration of a seated position of the subject person or acquire information related to a movement of a head of the subject person.

The vestibule stimulation apparatus may include an acknowledgment unit that acknowledges a user operation to select a sound stimulation for improving a motor function, improving a balance function, or enhancing an anti-aging benefit. When the acknowledgment unit acknowledges the user operation, the setting unit may set a sound stimulation for improving a motor function, improving a balance function, or enhancing an anti-aging benefit. The setting unit may set a sound stimulation for preventing or inhibiting motion sickness including travel sickness.

The vestibule stimulation apparatus may further include a position identification unit that identifies a position of the subject person relative to the sound generation unit. The setting unit may determine the sound volume level output from the sound generation unit in accordance with the position of the subject person. The setting unit may determine the sound volume level output from the sound generation unit such that the sound volume level at a position where the subject person is positioned is of a value between 70 and 85 decibels. The setting unit may control an output of the sound generation unit such that sound volume levels for stimulating left and right ear stones of the subject person are substantially equal. The sound generation unit may include a first sound generation unit that generates a sound stimulation toward one of ears of the subject person, and a second sound generation unit that generates a sound stimulation toward the other ear of the subject person. The setting unit may control an output of the first sound generation unit and an output of the second sound generation unit independently.

Another embodiment of the present disclosure relates to a program including computer-implemented modules including: a sound stimulation setting module that sets a sound stimulation having a sound volume level of a value between 70 and 85 decibels and a frequency of a value between 20 and 140 hertz, as a sound stimulation for activating a vestibular function via an ear stone of a subject person; and a sound stimulation generation module that generates the sound stimulation thus set.

The program may include a computer-implemented information acquisition module that acquires information related to the vestibular function of the subject person. The sound stimulation setting module may include a module that sets at least one of the sound volume level or a frequency of the sound stimulation in accordance with the information related to the vestibular function thus acquired. The information acquisition module may include a module that acquires status information representing a status of a current vestibular function.

The sound generation module may include a module that limits a time for which a sound is generated within a prescribed time frame to be a predetermined period of time or shorter. Further, the sound generation module may include a module that generates a preset sound stimulation while music data is being played back. The sound stimulation setting module may include a module capable of setting a sound stimulation suited to a plurality of types of modes. The program may further include a computer-implemented module that acknowledges a user operation to select one of a plurality of types of modes, and the sound stimulation setting module may include a module that sets a sound stimulation suited to a mode selection operation acknowledged.

INDUSTRIAL APPLICABILITY

The present disclosure relates to a technology for improving balance function and motor function of people by sound stimulation.

REFERENCE SIGNS LIST

1 . . . vestibule stimulation apparatus, 1a . . . vehicle-mounted vestibule stimulation apparatus, 2 . . . user operation acknowledgment unit, 3 . . . setting unit, 4 . . . sound generation unit, 5 . . . information acquisition unit, 6 . . . position identification unit, 7 . . . noise cancellation unit

The invention claimed is:

1. A vestibule stimulation apparatus comprising:
a control device that sets a sound stimulation; and
a sound generation device that generates the sound stimulation thus set, wherein
the control device sets the sound stimulation having a sound volume level of a value between 70 and 85 decibels and a frequency of a value between 50 and 140 hertz, as the sound stimulation for activating a vestibular function via an ear stone of a subject person.

2. The vestibule stimulation apparatus according to claim 1, further comprising:
an information acquisition device that acquires information related to the vestibular function of the subject person, wherein the control device sets at least one of the sound volume level or the frequency of the sound stimulation in accordance with the information related to the vestibular function thus acquired.

3. The vestibule stimulation apparatus according to claim 2, wherein
the information acquisition device acquires status information representing a status of a current vestibular function.

4. The vestibule stimulation apparatus according to claim 2, wherein
the information acquisition device acquires a duration of a seated position of the subject person.

5. The vestibule stimulation apparatus according to claim 2, wherein
the information acquisition device acquires information related to a movement of a head of the subject person.

6. The vestibule stimulation apparatus according to claim 1, comprising:
an acknowledgment device that acknowledges a user operation to select the sound stimulation for improving a motor function, improving a balance function, or enhancing an anti-aging benefit, wherein
when the acknowledgment device acknowledges the user operation, the control device sets the sound stimulation for improving a motor function, improving a balance function, or enhancing an anti-aging benefit.

7. The vestibule stimulation apparatus according to claim 1, wherein
the control device sets the sound stimulation for preventing or inhibiting motion sickness.

8. The vestibule stimulation apparatus according to claim 1, further comprising:
a position identification device that identifies a position of the subject person relative to the sound generation device, wherein
the control device determines the sound volume level output from the sound generation device in accordance with the position of the subject person.

9. The vestibule stimulation apparatus according to claim 1, wherein
the control device determines the sound volume level output from the sound generation device such that the sound volume level at a position where the subject person is positioned is of a value between 70 and 85 decibels.

10. The vestibule stimulation apparatus according to claim 1, wherein
the control device controls an output of the sound generation device such that sound volume levels for stimulating left and right ear stones of the subject person are substantially equal.

11. The vestibule stimulation apparatus according to claim 1, wherein
the sound generation device includes a first sound generation device that generates the sound stimulation toward one of the ears of the subject person, and a second sound generation device that generates the sound stimulation toward the other ear of the subject person, and
the control device controls an output of the first sound generation device and an output of the second sound generation device independently.

12. A dizziness treatment apparatus comprising the vestibule stimulation apparatus according to claim 1.

13. A health promotion apparatus comprising:
the vestibule stimulation apparatus according to claim 1; and
a chamber that accommodates the subject person.

14. A non-transitory, computer readable storage medium containing a program, which when executed by a computer, performs steps comprising:
a sound stimulation setting step that sets a sound stimulation having a sound volume level of a value between 70 and 85 decibels and a frequency of a value between 50 and 140 hertz, as the sound stimulation for activating a vestibular function via an ear stone of a subject person; and
a sound stimulation generation step that generates the sound stimulation thus set.

15. The non-transitory, computer readable storage medium containing the program according to claim 14, wherein the program further comprises a computer-implemented information acquisition step that acquires information related to the vestibular function of the subject person, wherein
the sound stimulation setting step further sets at least one of the sound volume level or the frequency of the sound stimulation in accordance with the information related to the vestibular function thus acquired.

16. The non-transitory, computer readable storage medium containing the program according to claim 15, wherein the information acquisition step further acquires status information representing a status of a current vestibular function.

17. The non-transitory, computer readable storage medium containing the program according to claim 14, wherein
the sound stimulation generation step further limits a time for which a sound is generated within a prescribed time frame to be a predetermined period of time or shorter.

18. The non-transitory, computer readable storage medium containing the program according to claim 14, wherein
the sound stimulation generation step further generates a preset sound stimulation while music data is being played back.

19. The non-transitory, computer readable storage medium containing the program according to claim 14, wherein
the sound stimulation setting step further sets the sound stimulation suited to a plurality of types of modes.

20. The non-transitory, computer readable storage medium containing the program according to claim 19, wherein the program further comprises a computer-implemented step that acknowledges a user operation to select one of a plurality of types of modes, wherein
the sound stimulation setting step further sets the sound stimulation suited to a mode selection operation acknowledged.

* * * * *